(12) United States Patent
Bernstein et al.

(10) Patent No.: US 10,588,746 B2
(45) Date of Patent: Mar. 17, 2020

(54) EXPANDABLE IMPLANTABLE CONDUIT

(71) Applicant: CARNEGIE MELLON UNIVERSITY, Pittsburgh, PA (US)

(72) Inventors: C. Douglas Bernstein, Pittsburgh, PA (US); Arush Kalra, Pittsburgh, PA (US)

(73) Assignee: CARNEGIE MELLON UNIVERSITY, Pittsburgh, PA (US)

(*) Notice: Subject to any disclaimer, the term of this patent is extended or adjusted under 35 U.S.C. 154(b) by 0 days.

(21) Appl. No.: 14/773,048

(22) PCT Filed: Mar. 7, 2014

(86) PCT No.: PCT/US2014/021814
§ 371 (c)(1),
(2) Date: Sep. 4, 2015

(87) PCT Pub. No.: WO2014/138599
PCT Pub. Date: Sep. 12, 2014

(65) Prior Publication Data
US 2016/0015516 A1    Jan. 21, 2016

Related U.S. Application Data

(60) Provisional application No. 61/851,487, filed on Mar. 8, 2013.

(51) Int. Cl.
*A61F 2/24* (2006.01)
*G05B 19/4099* (2006.01)
*A61F 2/30* (2006.01)

(52) U.S. Cl.
CPC .............. *A61F 2/2475* (2013.01); *A61F 2/24* (2013.01); *A61F 2/2412* (2013.01);
(Continued)

(58) Field of Classification Search
CPC .............................................. A61F 2002/30706
See application file for complete search history.

(56) References Cited

U.S. PATENT DOCUMENTS 4,160,688 A    7/1979 Brooks et al.
4,187,390 A    2/1980 Gore
(Continued)

FOREIGN PATENT DOCUMENTS

JP      S6446468 A      2/1989
JP      2007-536951 A   12/2007
(Continued)

OTHER PUBLICATIONS

Catanese et al. "Mechanical Properties of Medical Grade Expanded Polytetrafluoroethylene: The Effect of Internodal Distance, Density, and Displacement Rate". Apr. 24, 1998. Journal of Biomedical Materials Research, 48: 187-192.*
(Continued)

*Primary Examiner* — Jacqueline Woznicki
(74) *Attorney, Agent, or Firm* — Pepper Hamilton LLP (57) ABSTRACT

An expandable valved conduit for pediatric right ventricular outflow tract (RVOT) reconstruction is disclosed. The valved conduit may provide long-term patency and resistance to thrombosis and stenosis. The valved conduit may enlarge radially and/or longitudinally to accommodate the growing anatomy of the patient. Further, a method is disclosed for the manufacture of the valved conduit based in part on a plastically deformable biocompatible polymer and a computer-optimized valve design developed for such an expandable valved conduit.

17 Claims, 8 Drawing Sheets

(52) U.S. Cl.
CPC ........ *A61F 2/2418* (2013.01); *G05B 19/4099* (2013.01); *A61F 2/2415* (2013.01); *A61F 2002/30706* (2013.01); *A61F 2210/0004* (2013.01); *A61F 2220/0075* (2013.01); *A61F 2250/006* (2013.01); *A61F 2250/0007* (2013.01); *G05B 2219/42155* (2013.01)

(56) References Cited

U.S. PATENT DOCUMENTS

| | | | |
|---|---|---|---|
| 4,475,972 A * | 10/1984 | Wong | A61F 2/06 156/167 |
| 4,610,688 A * | 9/1986 | Silvestrini | A61F 2/06 623/1.53 |
| 4,955,899 A | 9/1990 | Della Corna et al. | |
| 5,443,499 A * | 8/1995 | Schmitt | A61F 2/06 623/1.13 |
| 5,466,261 A * | 11/1995 | Richelsoph | A61F 2/36 606/60 |
| 5,469,868 A | 11/1995 | Reger | |
| 5,800,512 A | 9/1998 | Lentz et al. | |
| 5,804,011 A | 9/1998 | Dutta et al. | |
| 5,843,161 A * | 12/1998 | Solovay | A61F 2/07 606/191 |
| 6,016,848 A | 1/2000 | Egres, Jr. | |
| 6,436,135 B1 | 8/2002 | Goldfarb | |
| 6,517,571 B1 | 2/2003 | Brauker et al. | |
| 6,716,239 B2 | 4/2004 | Sowinski et al. | |
| 6,863,686 B2 | 3/2005 | Shannon et al. | |
| 6,939,372 B2 | 9/2005 | Dong | |
| 7,153,324 B2 | 12/2006 | Case et al. | |
| 7,306,729 B2 | 12/2007 | Bacino et al. | |
| 7,789,908 B2 | 9/2010 | Sowinski et al. | |
| 8,672,997 B2 | 3/2014 | Drasler et al. | |
| 8,900,652 B1 | 12/2014 | Caballero et al. | |
| 2001/0039450 A1 * | 11/2001 | Pavcnik | A61F 2/01 623/1.24 |
| 2002/0055775 A1 | 5/2002 | Carpentier et al. | |
| 2002/0138135 A1 | 9/2002 | Duerig et al. | |
| 2003/0027332 A1 | 2/2003 | Lafrance et al. | |
| 2003/0114924 A1 | 6/2003 | Moe | |
| 2003/0139805 A1 | 7/2003 | Holmberg et al. | |
| 2003/0191525 A1 | 10/2003 | Thornton | |
| 2005/0075727 A1 | 4/2005 | Wheatley | |
| 2005/0096734 A1 | 5/2005 | Majercak et al. | |
| 2005/0137682 A1 | 6/2005 | Justino | |
| 2005/0228495 A1 | 10/2005 | Macoviak | |
| 2005/0240262 A1 | 10/2005 | White | |
| 2005/0283224 A1 * | 12/2005 | King | A61F 2/06 623/1.13 |
| 2006/0122693 A1 | 6/2006 | Biadillah et al. | |
| 2006/0149366 A1 | 7/2006 | Henderson | |
| 2006/0161248 A1 | 7/2006 | Case et al. | |
| 2006/0229716 A1 | 10/2006 | Mitrev | |
| 2006/0259136 A1 | 11/2006 | Nguyen et al. | |
| 2006/0265053 A1 | 11/2006 | Hunt | |
| 2006/0287717 A1 | 12/2006 | Rowe et al. | |
| 2007/0027528 A1 | 2/2007 | Agnew | |
| 2007/0043431 A1 | 2/2007 | Melsheimer | |
| 2007/0067021 A1 | 3/2007 | Haverkost et al. | |
| 2008/0206442 A1 | 8/2008 | Shekalim et al. | |
| 2009/0118826 A1 | 5/2009 | Khaghani | |
| 2010/0023120 A1 | 1/2010 | Holecek et al. | |
| 2010/0204775 A1 | 8/2010 | Edwin | |
| 2011/0060401 A1 * | 3/2011 | Hoerstrup | A61F 2/2418 623/1.16 |
| 2011/0071625 A1 | 3/2011 | Hill et al. | |
| 2011/0094592 A1 | 4/2011 | Cheng et al. | |
| 2011/0098800 A1 | 4/2011 | Braido et al. | |
| 2011/0125163 A1 | 5/2011 | Rutten et al. | |
| 2011/0166637 A1 | 7/2011 | Irwin et al. | |
| 2012/0158125 A1 * | 6/2012 | Obradovic | A61F 2/91 623/1.16 |
| 2012/0271396 A1 * | 10/2012 | Zheng | A61F 2/915 623/1.2 |
| 2012/0290082 A1 | 11/2012 | Quint et al. | |
| 2013/0013058 A1 | 1/2013 | Umezu et al. | |
| 2013/0166016 A1 | 6/2013 | Cully et al. | |
| 2013/0184807 A1 | 7/2013 | Kovach et al. | |
| 2014/0031924 A1 * | 1/2014 | Bruchman | A61F 2/24 623/2.11 |
| 2014/0031927 A1 | 1/2014 | Bruchman et al. | |
| 2014/0131268 A1 | 5/2014 | Abusleme et al. | |
| 2014/0155995 A1 | 6/2014 | Sun et al. | |
| 2014/0288642 A1 | 9/2014 | Yoshida | |
| 2014/0330372 A1 | 11/2014 | Weston et al. | |
| 2015/0366664 A1 | 12/2015 | Guttenberg et al. | |
| 2016/0067038 A1 | 3/2016 | Park et al. | |
| 2016/0100939 A1 | 4/2016 | Armstrong et al. | |
| 2017/0252156 A1 | 2/2017 | Bernstein et al. | |
| 2017/0196685 A1 | 7/2017 | Yoshida et al. | |
| 2018/0098844 A1 | 4/2018 | Bernstein et al. | |
| 2018/0098845 A1 | 4/2018 | Bernstein et al. | |

FOREIGN PATENT DOCUMENTS

| | | |
|---|---|---|
| JP | 2008526366 A | 7/2008 |
| WO | WO 1994/15548 A1 | 7/1994 |
| WO | WO 2009/061419 A1 | 5/2009 |
| WO | 2009134701 A2 | 11/2009 |
| WO | 2012018779 A2 | 2/2012 |
| WO | WO2013/019756 A2 | 2/2013 |
| WO | 2014145811 A1 | 9/2014 |
| WO | WO 2014/138599 A1 | 9/2014 |
| WO | 2018071417 A1 | 4/2018 |

OTHER PUBLICATIONS

Angioplasty Balloons from Advanced Polymers from MedDevice Online, accessed Oct. 3, 2019 (Year: 2019).*

Teleflex Medical OEM Balloons and Balloon catheters, accessed Oct. 3, 2019 (Year: 2015).*

BD Bard Conquest PTA Dilation Catheters, accessed Oct. 3, 2019 (Year: 2018).*

Nordston Medical, Medical Balloon types and specifications, accessed Oct. 3, 2019 (Year: 2018).*

Ando et al., Ten-year experience with handmade trileaflet polytetrafluoroethylene valved conduit used for pulmonary reconstruction, *J Thorac Cadiovasc Surg*, (2009), 137:124-131.

Batlivala et al., Pulmonary Valve Replacement Function in Adolescents: A Comparison of Bioprosthetic Valves and Homograft Conduits, *Ann Thorac Surg*, (2012), 93:2007-2016.

Bernstein et al., Bicuspid-Valved PTFE Conduit Optimization for Pediatric RVOT Reconstruction, Bioengineering Conference (NEBEC), (2011).

Bianca et al., Sex ratio imbalance in transposition of the great arteries and possible agricultural environmental risk factors, *Images Paediatr Cardiol*, (2001), 8:10-14.

Bielefeld et al., Reoperative Homograft Right Ventricular Outflow Tract Reconstruction, *Ann Thorac Surg*, (2001), 71(2):482-488.

Boethig et al., Mid term course after pediatric right ventricular outflow tract reconstruction: a comparison of homografts, porcine xenografts and Contegras, *European Journal of Cardio-thoracic Surgery*, (2005), 27:58-66.

Boudjemline et al., Use of bovine jugular vein to reconstruct the right ventricular outflow tract: Early results, *J Thorac Cardiovasc Surg*, (2003), 126:490-497.

Brown et al., Right ventricular outflow tract reconstruction with polytetrafluoroethylene monocusp valve: A twelve-year experience, *J Thorac Cardiovasc Surg*, (2007), 133(5):1336-1343.

Caldarone et al., Independent Factors Associated with Longevity of Prosthetic Pulmonary Valves and Valved Conduits, *J Thorac Cardiovasc Surg*, (2000), 120:1022-1031.

Canfield et al., National Estimates and Race/Ethnic-Specific Variation of Selected Birth Defects in the United States, *Birth Defects Research (Part A): Clinical and Molecular Teratology*, (2006), 76:747-756.

Chrysosotomou et al., Chapter 21: Tetralogy of Fallot with Pulmonary Atresia, *Critical Care of Children with Heart Disease: Basic Medical and Surgical Concepts*, (2010), 213-219.

(56) References Cited

OTHER PUBLICATIONS

Chrysosotomou et al., Chapter 22: Pulmonary Atresia with Intact Interventricular Septum, *Critical Care of Children with Heart Disease: Basic Medical and Surgical Concepts*, (2010), 221-229.
Cruz et al., Truncus Arteriosus, Chapter 35, Critical Care of Children with Heart Disease, Springer, (2009).
DeFrances et al., National Hospital Discharge Survey: 2005 annual summary with detailed diagnosis and procedure data, *National Center for Health Statistics, Vital Health Stat* (2007), 13(165):1-218.
Dur et al., In Vitro Evaluation of Right Ventricular Outflow Tract Reconstruction With Bicuspid Valved Polytetrafluoroethylene Conduit, *Artificial Organs*, (2010), 34: 1010-1016.
Erek et al., Durability of Stentless Bioprostheses for Right Ventricular Outflow Tract Reconstruction, *Ann Thorac Surg*, (2005), 79(6): 2202-2203.
Forbess et al., Conduit selection for right ventricular outflow tract reconstruction: contemporary options and outcomes, *Semin Thorac Cardiovasc Surg Pediatr Card Surg Annu*, (2004), 7:115-124.
Forbess et al., Cryopreserved Homografts in the Pulmonary Position: Determinants of Durability, *Ann Thorac Surg*, (2001), 71(1):54-59.
Fung, Biodynamics-circulation, Springer-verlag, New York-Berlin-Heidelberg-Tokyo 1984, 404 p. 189.
Gober et al., Adverse Mid-Term Outcome Following RVOT Reconstruction Using the Contegra Valved Bovine Jugular Vein, *Ann Thorac Surg*, (2005), 79:625-631.
Graham et al, Comparison of Norwood Shunt Types: Do the Outcomes Differ 6 Years Later?, *Ann Thorac Surg*, (2010), 90:31-35.
Hamilton et al., Births: Preliminary Data for 2009, *National Vital Statistics Reports*, (Dec. 21, 2010), 59(3):1-19.
Heron et al., Deaths: Final Data for 2006, *National Vital Statistics Reports*, (Apr. 17, 2009), 57(14):1-135.
Hoffman, Chapter 21: Congenital Heart Disease, *Essential Cardiology: Principles and Practice, 2$^{nd}$ Ed.*, 393-406.
Hoffman, The Incidence of Congenital Heart Disease, *J. Am. Coll. Cardiol.*, (2002), 39(12):1890-1900.
Hoyert et al., Annual Summary of Vital Statistics: 2004, *Pediatrics*, (2006):168-183.
International Search Report and Written Opinion for PCT/US2014/021814 dated Jun. 25, 2014.
International Search Report and Written Opinion for PCT/US2012/048902 dated Oct. 5, 2012.
Kaza et al., Long-term results of right ventricular outflow tract reconstruction in neonatal cardiac surgery: Options and outcomes, *J Thorac Cardiovasc Surg*, (2009), 138:911-916.
Menon et al., Regional Myocardial Dysfunction following Norwood with Right Ventricle to Pulmonary Artery Conduit in Patients with Hypoplastic Left Heart Syndrome, *Journal of the American Society of Echocardiography*, (2011), 24(8):827-833.
Meyns et al., The Contegra conduit in the right ventricular outflow tract induces supravalvular stenosis, *J Thorac Cardiovasc Surg*, (2004), 128:834-840.
Miyazaki et al., Expanded polytetrafluoroethylene conduits and patches with bulging sinuses and fan-shaped valves in right ventricular outflow tract reconstruction: Multicenter study in Japan, *J Thorac Cardiovasc Surg*, (2011), 142:1122-1129.
Naheed et al., Chapter 16 Pulmonary Atresia with Intact Ventricular Septum, *Heart Diseases in Children: A Pediatrician's Guide*, (2011), 195-202.
Niwa et al., Progressive Aortic Root Dilation in Adults and Late After Repair of Tetralogy of Fallot, *Circulation*, (2002), 106:1374-1378.
Ohye, Comparison of Right Ventricle to Pulmonary Artery Conduit and Modified Blalock-Taussig Shunt Hemodynamics After the Norwood Operation, Ann Thorac Surg, (2004), 78:1090-1093.
Oury, The Ross Procedure: Currently Registry Results, *Ann Thorac Surg*, (1998), 66:S162-S165.
Parker et al., Updated National Birth Prevalence Estimates for Selected Birth Defects in the United States, 2004-2006, *Birth Defects Research (Part A): Clinical and Molecular Tetratology*, (2010), 88:1008-1016.
Proptopapas et al., Contegra conduit for reconstruction of the right ventricular outflow tract: a review of published early and mid-time results, *Journal of Cardiothoracic Surgery*, (2008), 3:62 (7 pages).
Rosti et al., Mechanical valves in the pulmonary position: a reappraisal, *J Thorac Cardiovasc Surg*, (1998), 115(5):1074-1079.
Sano et al., Right ventricle-pulmonary artery shunt in first-stage palliation of hypoplastic left heart syndrome, *J Thorac Cardiovasc Surg*, (2003), 126:504-510.
Schreiber et al., Early Graft Failure of Small-Sized Porcine-Valved Conduits in Reconstruction of Right Ventricular Outflow Tract, *Ann Thorac Surg*, (2006), 82:179-186.
Shebani et al., Right ventricular outflow tract reconstruction using Contegra valved conduit: natural history and conduit performance under pressure, *European Journal of Cardio-thoracic Surgery*, (2006), 29:397-405.
Shiose et al., Recent Advances and Patents on Circulatory Support Devices for Pediatric Patients, *Recent Patents on Biomedical Engineering*, (2009), 2:161-164.
Stefano et al., Right ventricle outflow tract reconstruction in the pediatric population: A comparative analysis between different grafts, The 15$^{th}$ Congress on Cardio-Thoracic Surgery, (Nov. 2010).
Wald et al., Refining the assessment of pulmonary regurgitation in adults after tetralogy of Fallot repair: should we be measuring regurgitant fraction or regurgitant volume?, *European Heart Journal*, (2009), 30:356-361.
Wang et al., In vivo degradation characteristics of poly(glycerol sebacate), J Biomed Mater Res A, (2003), 66A:192-197.
Yoganathan et al., Fluid mechanics of heart valves, Annu Rev Biomed Eng, (2004), 6:331-362.
Yoshida et al., Midterm results of bicuspid valved PTFE conduit for right ventricular outflow tract reconstruction, *The 48th Annual Meeting of STS* (2012).
Yoshida et al., Right Ventricular Outflow Tract Reconstruction with Bicuspid Valved Polytetrafluoroethylene Conduit, *Annals of Thoracic Surgery*, (2011), 91:1235-1239.
Yuan et al., Right ventricular outflow tract reconstruction: valve conduit of choice and clinical outcomes, *J Cardiovasc Med*, (2008), 9(4):327-337.
International Search Report and Written Opinion for International Patent Application No. PCT/US2013/027103 dated Apr. 23, 2013.
International Search Report and Written Opinion for PCT/US2017/020421 dated May 18, 2017.
International Search Report and Written Opinion for International application No. PCT/US2017/055939, dated Feb. 5, 2018.
Canadian Office Actien dated Jul. 19, 2018 for Canadian Patent Application No. 2,855,943.
International Search Report and Written Opinion for PCT/US2016/038302 dated Sep. 7, 2016.

\* cited by examiner

EXPANDABLE IMPLANTABLE CONDUIT

CLAIM OF PRIORITY

This application is a U.S. national stage filing under 35 U.S.C. § 371 of International Application No. PCT/US2014/021814 filed Mar. 7, 2014 entitled "EXPANDABLE IMPLANTABLE CONDUIT," which claims priority of U.S. Provisional Application No. 61/851,487 filed on Mar. 8, 2013 entitled "Expandable Valve Conduit for Pediatric Right Ventricular Outflow Tract (RVOT) Reconstruction", the disclosures of which are incorporated herein by reference in their entirety.

BACKGROUND

Conduit selection for right ventricle outflow tract ("RVOT") reconstruction presents a challenge in the treatment of many congenital heart diseases including tetralogy of Fallot with pulmonary atresia, truncus arteriosus, transposition of great arteries with pulmonary stenosis, congenital aortic stenosis/insufficiency, and variants of such conditions. After the invention of the cryopreservation process in early 1980s, and especially with the increased availability of a wide range in graft sizes, homografts have become the conduit of choice for physicians performing RVOT reconstruction procedures. Such homografts, in many instance, may be used to replace Dacron conduit-mounted stented glutaraldehyde-treated porcine aortic valve heterografts. However, longitudinal studies have demonstrated that homografts may also require conduit replacement due to stenosis, shrinkage, calcification, and insufficiency, especially for younger patients.

Recently, xenograft designs have been evaluated for RVOT reconstruction. Non-limiting examples of such xenografts may include glutaraldehyde-fixed porcine aortic valves and roots, and glutaraldehyde-fixed segments of bovine jugular veins including venous valves. Although the anatomical shape of porcine aortic valves may prove useful in RVOT procedures, stenosis and calcification issues may still persist when such xenografts are implanted in children. Similarly, early fibrotic rind formation at the distal anastomosis, as well as significant conduit dilation and regurgitation may occur following the use of the bovine jugular veins. Thus, allografts and xenografts may prove to be insufficient replacements in RVOT procedures due to their poor hemodynamic performance and recurrent stenosis/insufficiency, especially in very young patients. As a result, multiple RVOT surgeries may be required until the pediatric patient reaches adulthood.

Implanted artificial (that is, non-biological) valves may require fewer replacement surgeries than valves having a biological origin. However, such artificial valves may require significant anticoagulant therapy, especially for valves placed in the pulmonary blood stream. Additionally, replacement artificial valves for use in pediatric/neonatal populations may be limited due to the need to custom design the valves based on intensive bioengineering studies. It may be appreciated, therefore, that there is a need for valved conduits with extended durability, especially for younger patients.

An expanded polytetrafluoroethylene (hereafter, ePTFE) valved conduit for pediatric RVOT reconstruction may include a valve design based on the surgical experience of a physician, or the results from a computer-optimization routine specific for non-expansible conduits.

Such non-expansible conduits can provide good functionality and resistance to thrombosis, stenosis, and calcification. However, the non-expansible conduit may not be capable of accommodating the changes in anatomical structures during patient growth. Somatic growth in pediatric patients can result in the need for replacement of implanted heart valves due to stenosis and other complications if the conduit or a valved conduit is not able to accommodate the anatomic or physiological changes due to patient growth.

At present, there appears to be no conduits for the reconstruction of a pediatric patient's right ventricular outflow tract (RVOT) having long-term patency, a functional valve, and no thrombogenicity. Anti-thrombogenic materials and optimal valve designs can produce good initial results. However, young children may quickly outgrow the implanted conduits and may require reoperation and replacement. To date, only tissue-engineered conduits or valved conduits have been proposed to accommodate patient growth, but these solutions are time- and cost-intensive and still generally unproved for long-term functionality.

SUMMARY

In some embodiments, an implantable device may include a conduit composed of a plastically deformable material having a yield strength of about 0.1 MPa to about 4 MPa and an ultimate tensile strength greater than about 4 MPa.

In some embodiments, a valved conduit may include a conduit and a valve structure disposed therein, in which the conduit is composed of at least one plastically deformable material having a yield strength of about 0.1 MPa to about 4 MPa and an ultimate tensile strength greater than about 4 MPa.

In some embodiments, a method of fabricating a valved conduit composed of a plastically deformable material for implantation into an animal may include obtaining at least one datum dependent at least in part on one or more anatomical structures or physiological functions of the animal, determining an initial radial dimension of the valved conduit, and determining an at least one expansion measurement for the conduit dependent at least in part on a change in the one or more anatomical structures or physiological functions. The plastically deformable material may have a yield strength of about 0.1 MPa to about 4 MPa and an ultimate tensile strength greater than about 4 MPa. The embodiments further may include calculating, using a computing device, an initial flow metric representative of a fluid flowing through an initial valved conduit having physical characteristics of an initial mathematical model of the valved conduit based at least in part on the at least one datum, the initial radial dimension, and an at least one plasticity property of the plastically deformable material. Additionally, the embodiments may include calculating, using the computing device, an at least second flow metric representative of the fluid flowing through a second valved conduit having physical characteristics of an at least second mathematical model of the valved conduit, based at least in part on the at least one datum, the expansion measurement, and the at least one plasticity property. Further, the embodiments may include calculating, using the computing device, a deformation metric based at least in part on the initial flow metric and the at least one second flow metric and fabricating the valved conduit based, at least in part, on the physical characteristics of the initial mathematical model of the valved conduit if the deformation metric is greater than or equal to an acceptance value.

In some embodiments, a method of replacing a first valved conduit composed of a plastically deformable material implanted in an animal may include contacting an inner surface of the first valved conduit with an expansion device, causing the expansion device to expand, thereby radially increasing at least a portion of the first valved conduit, introducing a second valved conduit within at least a portion of the first valved conduit, and causing the second valved conduit to expand within the at least portion of the first valved conduit, in which the plastically deformable material has a yield strength of about 0.1 MPa to about 4 MPa and an ultimate tensile strength greater than about 4 MPa.

DETAILED DESCRIPTION

Before the present methods are described, it is to be understood that this invention is not limited to the particular systems, methodologies or protocols described, as these may vary. It is also to be understood that the terminology used herein is for the purpose of describing particular embodiments only, and is not intended to limit the scope of the present disclosure which will be limited only by the appended claims.

For the purpose of this disclosure, the term "plastically deformable material" means a material that may change its shape, size, or both shape and size in response to a deforming force placed thereon, and which does not fully recover its original shape, size, or both shape and size once the deforming force has been removed.

For the purpose of this disclosure, the term "elastic material" means a material that may change its shape, size, or both shape and size in response to a deforming force placed thereon, and which recovers its original shape, size, or both shape and size once the deforming force has been removed.

For the purpose of this disclosure, the term "deforming force" means a force that, when applied to a material, will result in a change in the shape, size, or both shape and size of the material.

For the purpose of this disclosure, the term "yield strength" means the smallest deforming force that, when applied to a material, will result in a non-recoverable change in the shape, size, or both shape and size of the material.

For the purpose of this disclosure, the term "ultimate tensile strength" means the smallest deforming force that, when applied to a material, will result in a break or failure of the material.

For the purpose of this disclosure, the term "anatomic compliance" or "anatomically compliant" means the capability of a material or structure to change size, shape, or size and shape in response to the changes in anatomical structures (resulting from patient growth) within a patient in which the material or structure has been implanted.

For the purpose of this disclosure, the term "physiological compliance" or "physiologically complaint" means the capability of a material or structure to maintain its structural integrity under normal physiological conditions. As such, a physiologically compliant material or device may exhibit sufficient elasticity to allow the material or device to expand and return to its original shape under normal physiological conditions. For example, a physiologically compliant device designed to be incorporated into the circulatory system may exhibit elasticity similar to healthy blood vessels under normal physiological conditions.

Various embodiments of the invention are directed to implantable conduits that are physiologically compliant under physiological conditions but that can also plastically deform under non-physiological conditions allowing the conduit to be expanded radially and/or longitudinally. Such deformation allows for the conduit to be expanded to suit the patient's needs. For example, on implantation in a child or juvenile patient, such implantable conduits may have a first physiologically appropriate radius consistent with the patient's age, size, or physical condition. As the patient grows, the radius of the implantable conduit may be increased by applying sufficient radial force using, for example, a balloon catheter, to cause the implantable conduit to deform taking on a second physiologically appropriate radius. Alternatively, the radius of the implantable conduit may increase to a larger physiologically appropriate radius as a result of anatomical and/or physiological forces associated with patient growth as the patient grows. After stable expansion, the conduit will continue to be physiologically compliant under physiological conditions. Thus, the expandable conduit may be deformed to expand or grow with the patient, thereby reducing the need to invasive surgeries to replace the conduit as patient needs change.

The expandable conduit disclosed herein may also be useful for replacing previously implanted homograft or other conduits that have become dysfunctional or insufficient. Additional uses for the disclosed conduit may include applications related to the treatment of pediatric and adult disorders, including other areas of the heart or more generally to other parts of the body. Some examples of additional uses may further include procedures associated with repair of pediatric left ventricular outflow tract (LVOT) pathologies as well as for use in Fontan/Kreutzer procedures. It may be further understood that such expandable conduits may find use in non-human animals for veterinary purposes as well.

The expandable conduits of various embodiments may be composed, at least in part, of one or more biocompatible polymers that are plastically deformable under some conditions and are elastic under other conditions.

In particular, under some physiological conditions the conduit may be elastic. Typical blood flow exerts up to about 0.02 MPa of pressure on the blood vessels under stress conditions or high intensity activity. Under such conditions, the natural elasticity of the blood vessels allow them to radially expand to allow for increased blood flow. The blood vessels return to their normal diameter under lower steady state pressures. The expandable conduits of various embodiments exhibit similar elasticity. For example, in some embodiments, the conduits may be elastic at pressures of from about 0.0001 MPa to about 0.02 MPa, about 0.0001 MPa to about 0.015 MPa, about 0.0001 MPa to about 0.004 MPa, or any individual pressure or range encompassed by these example ranges.

The conduits of such embodiments may be deformable at non-physiological pressures greater than those described above. Therefore, as patient needs change, such conduits may be enlarged by applying pressures in excess of what would be produced by, for example, natural blood flow. In such embodiments, an expandable conduit that is elastic at the pressures described above may be radially deformed by use of a balloon catheter or other device. In various embodiments, such conduits may be plastically deformable at pressures (or yield strength) of, for example, about 0.05 MPa to about 2.5 MPa, about 0.3 MPa to about 2.5 MPa, about 0.1 MPa to about 4 MPa, or any range or individual pressure encompassed by these example ranges. It may be understood that specific yield strength values disclosed herein are not to be considered limiting, and that some embodiments of expandable conduits may include those having yield strength values greater than about 4 MPa. Conduits having such large yield strength values may be useful for use with expansion devices, such as balloon catheters, capable of exerting radial pressures greater than about 4 MPa.

In particular embodiments, the conduits may exhibit a yield strength that allows for expansion under certain physiological conditions. For example, in some embodiments, the expandable conduit may exhibit a yield strength of about 0.004 MPa to about 0.02 MPa, about 0.015 MPa to about 0.04 MPa, or any range or individual yield strength encompassed by these example ranges. Because such pressures are rarely achieved under physiological conditions, such conduits may slowly expand after implantation, and this slow expansion may allow for the conduit to expand with the growth of the patient reducing the need for manual expansion using a balloon catheter or other device.

In each of the embodiments described above, the conduits may typically exhibit an ultimate tensile strength that is greater than about 2.5 MPa, 3.0 MPa, 4.0 MPa, or 5.0 MPa. Such ultimate tensile strengths ensure that the conduit does not burst either under physiological conditions or at deformation pressures. In some alternative embodiments, a conduit may exhibit an ultimate tensile strength that is about 1 MPa greater than its yield strength. Non-limiting examples of such conduits may include a conduit having a yield strength of about 0.02 MPa and an ultimate tensile strength greater than about 1.0 MPa, a conduit having a yield strength of about 0.3 MPa and an ultimate tensile strength greater than about 1.3 MPa, a conduit having a yield strength of about 1.0 MPa and an ultimate tensile strength greater than about 2.0 MPa, a conduit having a yield strength of about 2.5 MPa and an ultimate tensile strength greater than about 3.5 MPa, and a conduit having a yield strength of about 4 MPa and an ultimate tensile strength greater than about 5 MPa.

Conduits fabricated from materials characterized by such combinations of yield strengths and ultimate tensile strengths may be implanted into vascular structures using sutures. It may be understood that additional strength characteristics of the conduits may be related to the suture retention strength. In some non-limiting examples, the suture retention strength may be greater than or about equal to 50 gram force (about 0.5 N). In some alternative non-limiting examples, the suture retention strength may be greater than or about equal to 80 gram force (about 0.8 N).

Embodiments of conduits having yield strengths and ultimate tensile strengths as disclosed above may be either compressed or expanded. Such compression or expansion may be provided along either the radial dimension or along the longitudinal dimension. In some examples, a conduit may exhibit a radial expandability of about 20% to about 200% above its initial pre-expansion radius. Examples of such percent radial expandability may include, without limitation, about 20%, about 40%, about 50%, about 100%, about 150%, and about 200% above the initial pre-expansion radius, and ranges between any two of these values (including endpoints). In some examples, a conduit may exhibit a radial compressibility of about 33% to about 83% of the initial pre-compression radius. Examples of such percent radial compressibility may include, without limitation, about 33%, about 40%, about 45%, about 50%, about 60%, about 70%, about 80%, and about 83% of the initial pre-compression radius, and ranges between any two of these values (including endpoints). In some alternative examples, a conduit may exhibit a longitudinal expandability of about 5% to about 500% above the initial pre-expansion length. Examples of such percent longitudinal expandability may include, without limitation, about 5%, about 10%, about 50%, about 100%, about 150%, about 200%, about 300%, about 400%, and about 500% above the initial pre-expansion length, and ranges between any two of these values (including endpoints). In some additional examples, a conduit may exhibit a longitudinal compressibility of about 33% to about 91% of the initial pre-compression length. Examples of such percent longitudinal compressibility may include, without limitation, about 33%, about 40%, about 50%, about 60%, about 70%, about 80%, about 90%, and about 91% of the initial pre-compression length, and ranges between any two of these values (including endpoints).

Embodiments of the above-disclosed conduit, possessing such elastic and plastic properties, may not be limited to any particular material, combination of materials, shape, size, or manner of manufacture. Non-limiting examples of such conduits may include other useful characteristics as disclosed below. The properties described above can be achieved using any means available in the art. For example, in some embodiments, materials with yield strengths of, for example, about 0.05 MPa to about 2.5 MPa, about 0.1 MPa to about 2.0 MPa, about 0.1 MPa to about 1.5 MPa, or any range or individual pressure encompassed by these example ranges, can be manufactured into conduits.

In some embodiments, the expandable conduit may be composed of one or more biocompatible materials, and in certain embodiments, the biocompatible material may be a fluoropolymer. Non-limiting examples of such biocompatible materials may include polytetrafluoroethylene, expanded polytetrafluoroethelyne (ePTFE), polyester, polyethylene terephthalate, polydimethylsiloxane, polyurethane, and/or combinations of those materials. Such biocompatible polymers may also be characterized by an intermode distance (IND), a measure of an average distance between nodes formed in a polymer network. In some examples, the biocompatible material used in expandable conduits may have an internode distance of about 10 μm to about 40 μm. In some alternative embodiments, the biocompatible material may have an internode distance of less than 200 μm. Examples of such an internode distance may include, without limitation, about 20 µm, about 40 µm, about 60 µm, about 80 µm, about 100 µm, about 120 µm, about 140 µm, about 160 µm, about 180 µm, about 200 µm, and ranges between any two of these values (including endpoints).

In various embodiments, such materials may have a density less than about 2 mg/mm$^3$. In some examples, the material may have a density of about 0.2 mg/mm$^3$ to about 2 mg/mm$^3$. In some alternative examples, the material may have a density of about 0.2 mg/mm$^3$ to about 0.5 mg/mm$^3$. Examples of such material density may include, without limitation, about 0.2 mg/mm$^3$, about 0.4 mg/mm$^3$, about 0.6 mg/mm$^3$, about 0.8 mg/mm$^3$, about 1.0 mg/mm$^3$, about 1.5 mg/mm$^3$, about 2.0 mg/mm$^3$, and ranges between any two of these values (including endpoints).

In some embodiments, the expandable conduit may be made of a polymer that has been coated with material having useful biomedical properties. In some additional embodiments, the conduit may incorporate bio-active coatings. Non-limiting examples of such bio-active coatings may include one or more anti-coagulant materials. Non-limiting examples of an anti-coagulant material may include a coumarin, heparin, a heparin derivative, a Factor Xa inhibitor, a direct thrombin inhibitor, hementin, sintered porous titanium microspheres, and/or combinations of those materials.

In some additional embodiments, the expandable conduit may be fabricated from a physically pre-treated material. Physical pre-treatment of the material may include longitudinal mechanical compression with heating. Further, additional material may be added during the pre-treatment process. The yield strength of a conduit fabricated from such pre-treated materials may depend on the final length or radius to which the conduit is expanded. For example, a conduit expanded either longitudinally or radially up to the original material length or radius (that is, length or radius of the material prior to compression/heating) may have a yield strength much less than that of the original material. As an example, the original material of a conduit may have a yield strength of about 10 MPa, but a conduit comprising such pre-treated material may have a yield strength of about 1 MPa for expansion up to about the original length or radius of material.

In some embodiments, the expandable conduit may be composed of multiple materials. For example, the conduit may be composed of a material having a first yield strength and first ultimate tensile strength and may be impregnated with a second material having a second yield strength and/or second ultimate tensile strength. In an additional non-limiting example, the conduit may be fabricated from two or more elastic or plastically deformable materials woven together.

In embodiments in which the expandable conduit includes more than one layer of material, each layer of a multi-layer conduit may be composed of the same material. In other embodiments, each layer of a multi-layer conduit may be composed of a different material. In further embodiments, each layer of a multi-layer conduit may be composed of a material characterized by different mechanical properties. For example, an inner layer of a multi-layer conduit may include a material having a first yield strength and first ultimate tensile strength and an outer layer that may include a second material having a second yield strength and/or second ultimate tensile strength. The first yield strength may be greater than, about equal to, or less than the second yield strength. The first ultimate tensile strength may be greater than, about equal to, or less than the second ultimate tensile strength. Alternatively, an inner layer may include an elastic or plastically deformable material and an outer layer may include an inelastic or frangible material.

Conduits composed of multiple layers may have expansion capabilities depending on the material properties of the multiple layers. For example, a conduit composed of a biodegradable outer layer and an elastic or plastically deformable inner layer may be expanded due to the force of a fluid flowing therein but only after the outer layer has degraded. In another example, a conduit having an inelastic or frangible outer layer and an elastic or plastically deformable inner layer may remain in an unexpanded state until sufficient force, for example supplied by an inserted expansion device, is applied internally to rupture the outer layer and thus permit the inner layer to expand.

It may be understood that the conduit materials, formulations, and/or mechanical properties may be constant over the longitudinal dimension of the conduit. Alternatively, the conduit materials, formulations, and/or mechanical properties of the conduit may vary along the length or any partial length of the conduit. Conduits having multiple branches may have mechanical properties that differ between the branches and/or a main cylindrical tube of the conduit.

In some examples, the conduit may form a generally cylindrical tube. In other examples, the conduit may have a more complex geometry including having branches. In some examples, the conduit may form a main cylindrical tube along a partial length of the conduit and then branch into two or more tubular portions. In alternative examples, the conduit may form a main cylindrical tube along the length of the conduit with tubular portions extending from the main cylindrical tube. It may be understood that a conduit disclosed as being composed of a "cylindrical tube" may include any number of bends, kinks, or other deformations along the longitudinal axis of the cylindrical tube.

The conduit may generally be any size or shape, including having a pre-expansion inner diameter greater than or equal to about 2 mm and less than about 20 mm. Examples of such pre-expansion inner diameter may include, without limitation, about 2 mm, about 4 mm, about 6 mm, about 8 mm, about 10 mm, about 15 mm, about 20 mm, and ranges between any two of these values (including endpoints). In some other examples, the conduit may have a pre-expansion inner diameter greater than or equal to about 4 mm and less than about 14 mm. Examples of such pre-expansion inner diameter may include, without limitation, about 4 mm, about 6 mm, about 8 mm, about 10 mm, about 12 mm, about 14 mm, and ranges between any two of these values (including endpoints). After expansion, the conduit may have an inner diameter greater than or equal to about 8 mm and less than about 24 mm. In other examples, after expansion, the conduit may have an inner diameter greater than or equal to about 4 mm and less than about 34 mm. Examples of such post-expansion inner diameter may include, without limitation, about 4 mm, about 6 mm, about 8 mm, about 10 mm, about 15 mm, about 20 mm, about 25 mm, about 30 mm, about 34 mm, and ranges between any two of these values (including endpoints). In some examples, the expandable conduit may be fabricated from a plastically deformable material having a thickness of about 0.01 mm to about 2 mm. In some examples, the conduit may have a wall thickness greater than or equal to about 10 µm and less than about 2000 µm. In other non-limiting example, the conduit may have a wall thickness of about 100 µm to about 1000 µm. Examples of such conduit wall thickness may include, without limitation, about 10 µm, about 20 µm, about 50 µm, about 100 µm, about 200 µm, about 500 µm, about 1000 µm, about 2000 µm, and ranges between any two of these values (including endpoints).

In some alternative embodiments, the mechanical properties of the expandable conduit may be about equal in or may differ between the longitudinal dimension and the radial dimension. In one example, an expandable conduit may have a first yield strength along the longitudinal dimension greater than 0.2 MPa, and a second yield strength along the radial dimension greater than 0.2 MPa. In an alternative example, the first yield strength in a longitudinal dimension of a conduit may be greater than about 10 MPa and the second yield strength in a radial dimension of the conduit may be greater than about 2.75 MPa.

In certain embodiments, the conduits described above may include additional components. For example, in some embodiments, the conduits may include a stent that is attached to or encapsulated by the material making up the conduit, or an inner layer may include a stent while an outer layer may include an elastic or plastically deformable material. In yet another example, a conduit may be composed of a biodegradable outer layer and an elastic or plastically deformable inner layer. In some further examples, a multi-layer expandable conduit may include a first inner layer comprising a woven material and a second outer layer comprising a woven material. It may be understood that the woven material composing the inner layer may be the same as the woven material composing the outer layer. Alternatively, the woven material composing the inner layer may differ from the woven material composing the outer layer.

Although disclosed above are conduits composed of a variety of materials and having a variety of mechanical properties associated therewith, it may be appreciated that such materials and properties may equally apply to conduits comprising a valve structure (hereafter, a valved conduit). In addition to valve structures, such implantable conduits may include one or more sinus bulge geometries. In some examples, a valved conduit may include one or more sinus bulges in a proximal (upstream to flow) portion with respect to a valve structure. Alternatively, a valved conduit may include one or more sinus bulges in a distal (downstream to flow) portion with respect to a valve structure. Such sinus bulge geometries included in a valved conduit may be fabricated due to the application of heat and/or pressure to at least a portion of the conduit. It may be further understood that a valved conduit composed of multiple layers may have the valve structure associated with an inner-most layer. Such valved conduits may also find use for implantation in animals for veterinary purposes.

Figure 1:
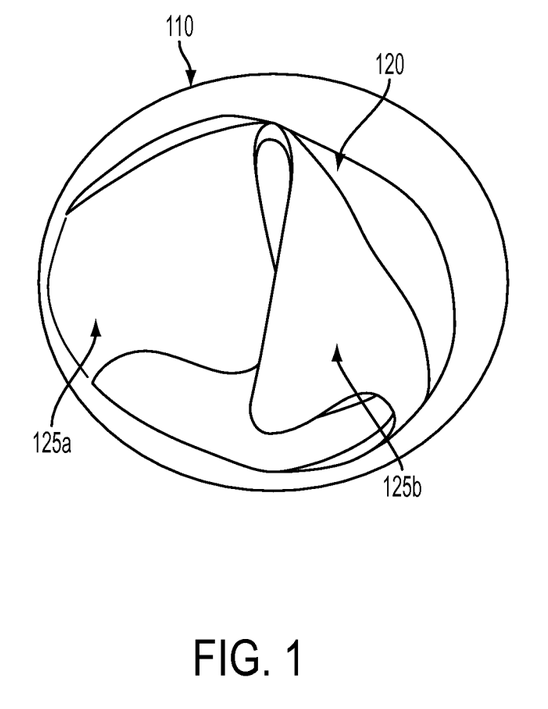
FIG. 1 illustrates an embodiment of a cross-section view of an expandable valved conduit with bicuspid leaflets prior to expansion in accordance with the present disclosure.

FIG. 1 depicts a cross sectional view of an expandable valved conduit that may be implantable in an animal or human, according to one non-limiting example. The expandable valved conduit may include a conduit 110 constructed of synthetic material and a valve structure 120. The valve structure 120 may include one or more leaflet elements 125a, 125b contained within the conduit 110. Each of one or more leaflet elements 125a, 125b may have one or more free edges capable of motion and one or more edges which may be in mechanical communication with the conduit 110. In some non-limiting examples, the edges in mechanical communication with the conduit 110 may be affixed to an inner conduit surface.

Figures 2A, 2B:
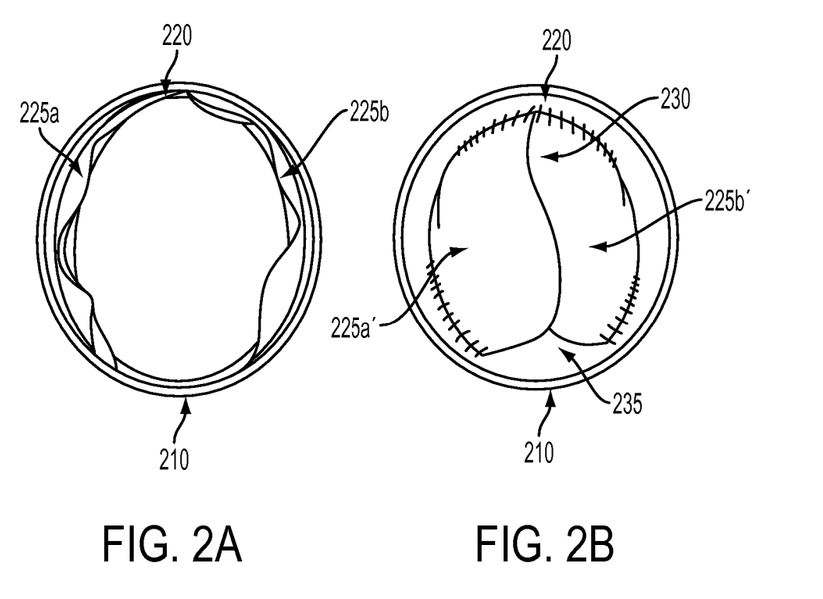
FIGS. 2A and 2B illustrate embodiments of an expandable valved conduit in an open and a closed position, respectively, in accordance with the present disclosure.

FIGS. 2A and 2B depict a cross section view of an example of an expandable valved conduit; FIG. 2A depicts the valved conduit in an open state, and FIG. 2B depicts the valved conduit in a closed state that may result in closing of the majority of the valve's open orifice area while retaining an open gap area.

Both FIGS. 2A and 2B illustrate a conduit 210 including a valve structure 220 therein. In the non-limiting example depicted in FIGS. 2A and 2B, the valve structure 220 may be composed of two leaflets 225a and 225b. It may be understood that alternative embodiments of a valve structure 220 may include one leaflet, three leaflets, or any number of leaflets. FIG. 2A depicts the valved conduit in an open state in which the valve leaflets 225a and 225b may be separated by some distance and may additionally lie at least in part along the inner surface of the conduit 210 due the force of fluid flow. In the open state, the valve leaflets 225a and 225b may be disposed to provide an open orifice area therebetween that may have an orifice area almost the same as the cross-sectional area of the conduit 210.

FIG. 2B depicts the valved conduit in a closed state. In the closed state, the valve leaflets 225a' and 225b' may be proximate to each other. In some non-limiting embodiments, the valve leaflets 225a' and 225b' may lie edge-to-edge with each other. In some other non-limiting embodiments, the valve leaflets 225a' and 225b' may at least partially overlap each other. In some other non-limiting embodiments, the valve leaflets 225a' and 225b' may be domed or partially domed. FIG. 2B illustrates other possible features associated with the valve structure 220. Such additional features may include a commissure 230 joining together at least a part of the valve leaflets 225a' and 225b', and a gap 235 between at least one free edge of at least one leaflet (225a', 225b', or both) and an inner surface of the conduit 210.

In general, a valve structure incorporated in a valved conduit may be constructed of the same material as those comprising the conduit, including, without limitation, a plastically deformable material, an elastic material, a non-deformable material, or mixtures thereof. In some examples, the valve structure may be composed of the same materials and have the same mechanical properties as the conduit. In some other examples, the valve structure may be composed of the same material as the conduit but have mechanical properties differing from those of the conduit. In some additional examples, the valve structure may be composed of materials that differ from those of the conduit. In one example, the conduit, valve structure, or both conduit and valve structure may be made of a polymer which has been coated with an anti-coagulant material. In some additional examples, the conduit, valve structure, or both conduit and valve structure may incorporate bio-active coatings.

In another embodiment, the valved conduit may include a conduit having a first conduit layer having an inner surface in physical communication with an outer surface of a second conduit layer and a valve structure is disposed within the second conduit layer. As one example of such a multi-layer valved conduit, the first conduit layer may be composed of a first plastically deformable material having a yield strength of about 0.1 MPa to about 4 MPa, and the second conduit layer may be composed of the same plastically deformable material as the first layer. In an alternative example, the multi-layer valved conduit may be composed of a first conduit layer having a first plastically deformable material having a yield strength of about 0.1 MPa to about 4 MPa, and a second conduit layer composed of a second material that may differ from the first material. In still another example, the valved conduit may have a first conduit layer composed of a woven material, a second conduit layer composed of a woven material, or both the first conduit layer and the second conduit layer may each be composed of a woven material. In some embodiments of the multi-layer valved conduit, the first conduit layer may be biodegradable. In some alternative embodiments of a multi-layer valved conduit, the first conduit layer may include a non-plastically deformable material. In yet another embodiment, the multi-layer valved conduit may include a stent as part of the second conduit layer.

In order to ensure that proper valve function is maintained throughout the lifetime of the conduit, including expansion, a computer-optimization routine is disclosed herein that may accurately and precisely simulate the geometry of different valve leaflet designs in varying positions and throughout different stages of conduit expansion. These leaflet geometries can be simulated under physiologic flow conditions through the use of computation fluid dynamics. Based on such simulations, an optimal leaflet may be designed to minimize regurgitation during ventricular diastole and maximize open orifice area during ventricular systole throughout the lifetime of the conduit.

Valve structures incorporated into valved conduits may be designed based at least in part on modeling/optimization algorithms embodied in a computing device. Such algorithms may be used to design valve structures capable of meeting one or more acceptance criteria regarding fluid flow through the valved conduit as the conduit radially enlarges. In one example, the modeling/optimization algorithms may use physical data from actual patients who might require the conduit. These modeling/optimization algorithms may include Computational Fluid Dynamics (CFD), solid-mechanics modeling, and other optimization routines. Acceptance criteria may include measures of fluid turbulence, regurgitation, and other dynamic parameters of the fluid flow through the valve structure as the conduit radially enlarges and the valve structure changes position within the conduit. Additional parameters related to structural components of the valved conduit may include the area of the valve structure orifice when in the open configuration, the fluid volume flow through the open valve structure, and a measure related to the physical contact of valve structure leaflets and an inner surface of the conduit.

Figure 3A:
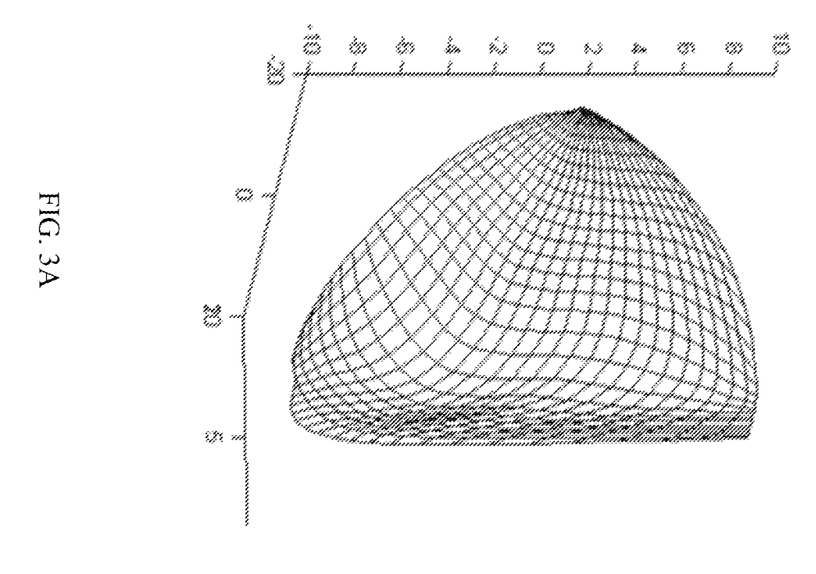
FIGS. 3A and 3B illustrate an embodiment of a model of a 20 mm conduit in mesh form, and after being converted to a solid 3D model, respectively, in accordance with the present disclosure.
Figure 3B:
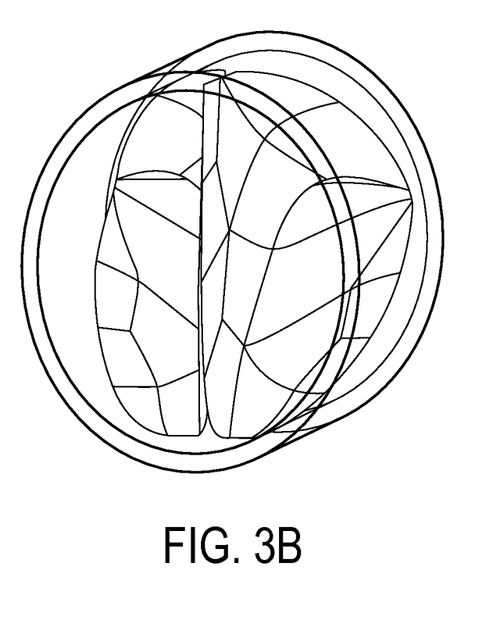

In one embodiment, modeling and/or optimization calculations may be used to reduce diastolic flow regurgitation through a heart valve structure, as well as to improve effective orifice area and overall heart valve structure function. In one non-limiting embodiment, a heart valve leaflet structure modeling program may predictively generate one or more heart valve leaflet structure models based, at least in part, on geometric parameters and solid-mechanics principals. In another non-limiting embodiment, one or more solid heart valve leaflet structure models may be analyzed according to one or more fluid flow analytical methods. For example, FIG. 3A depicts a mesh-structure model of a heart valve leaflet generated by a solid mechanical simulation algorithm; FIG. 3B depicts a solid model constructed from the mesh-structure in FIG. 3A.

Non-limiting examples of such fluid flow analytical methods may include fluid-structure interaction (FSI) and computational fluid dynamics (CFD) simulations. In a non-limiting embodiment, an iterative optimization method for generating heart valve leaflet structure models may include: (1) calculating a heart valve leaflet structure model based on a set of parameters including one or more geometric parameters; (2) analyzing a performance of the heart valve leaflet structure model based at least in part on one or more fluid flow analytical methods; (3) calculating a performance cost function according to data calculated by the one or more fluid flow analytical methods; and (4) varying one or more of the heart valve leaflet structure modeling parameters in a manner to minimize the value of the valve performance cost function.

Figure 4:
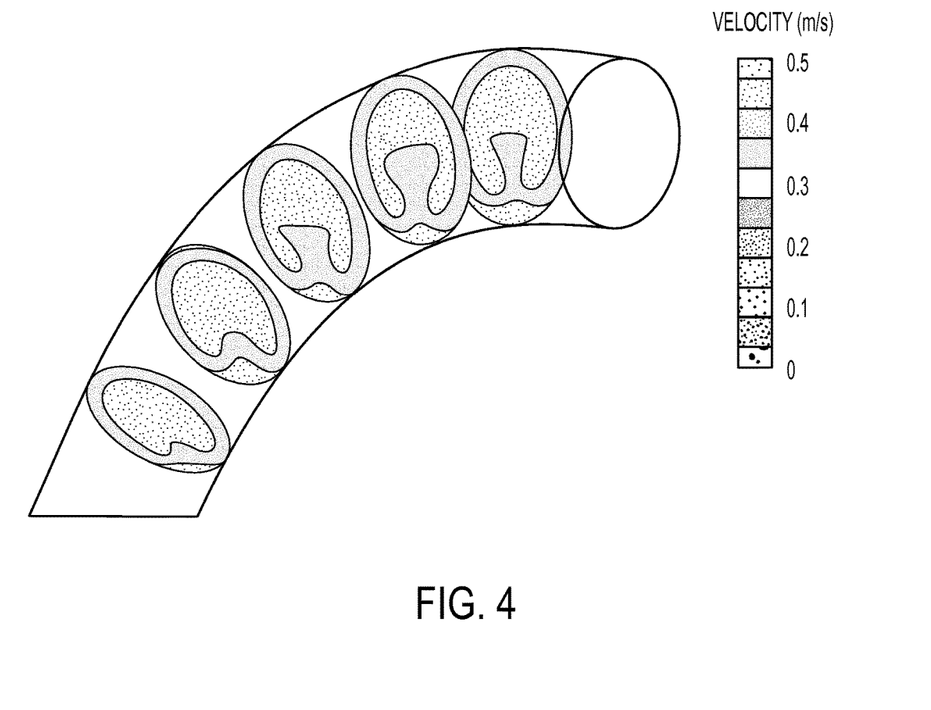
FIG. 4 illustrates an embodiment of a computational fluid dynamics simulation of flow through a 20 mm diameter curved conduit in the physiologic position in accordance with the present disclosure.

Mathematical modeling and/or optimization calculations that may be used to calculate shapes and/or dimensions of heart valve leaflet structures may include, without limitation, computational fluid dynamics (CFD), solid-mechanics modeling, fluid/structure interaction (FSI) modeling, and blood-flow optimization algorithms. Calculations based on CFD models may show a difference in blood flow velocity based on a curvature of the conduit component of a heart valve structure. FIG. 4 depicts an example of such a flow-velocity simulation. For example, a blood flow model may indicate greater flow along a conduit axis having a large radius of curvature as opposed to the blood flow in a conduit having a smaller radius of curvature. CFD models, for example, may provide data to suggest that a curved conduit should not have a heart valve leaflet structure at the conduit bottom as a heart valve leaflet structure lower leaflet may become stuck at the closing phase, thereby leading to thrombosis.

Mathematical calculations and/or optimization calculations may be carried out, for example, by means of one or more computing devices. Such computing devices may include, without limitation, one or more of the following: central processor units, numerical accelerators, static and/or dynamic memories, data storage devices, data input devices, data output devices, communication interfaces, and visual displays. While a single computing device may be used for such calculations, multiple computing devices, for example in a shared network or cloud configuration, may also be used. It may be appreciated that the one or more computing devices may operate independently or in concert. In addition, communications between one or more users and one or more computing devices may occur over one or more input interface device, including, without limitation, a keyboard, a mouse, a track-ball, a stylus, a voice recognition system, and/or a touch pad display. In addition, the one or more computing devices may provide output information to the one or more users by one or more output interface device, including, without limitation, a visual display, a printer, and/or an audio interface. Data communication between computing devices may occur over one or more computing system communication interface, including, but not limited to, a serial interface, a parallel interface, an Ethernet interface, a wireless interface, and/or an optical interface. Additional communications between computing devices, or between computing devices and users, may be accomplished over one or more computing system communication protocols including, but not limited to, a personal area networks (such as BlueTooth), a local area network, a wide area network, and/or a satellite network.

Figure 5:
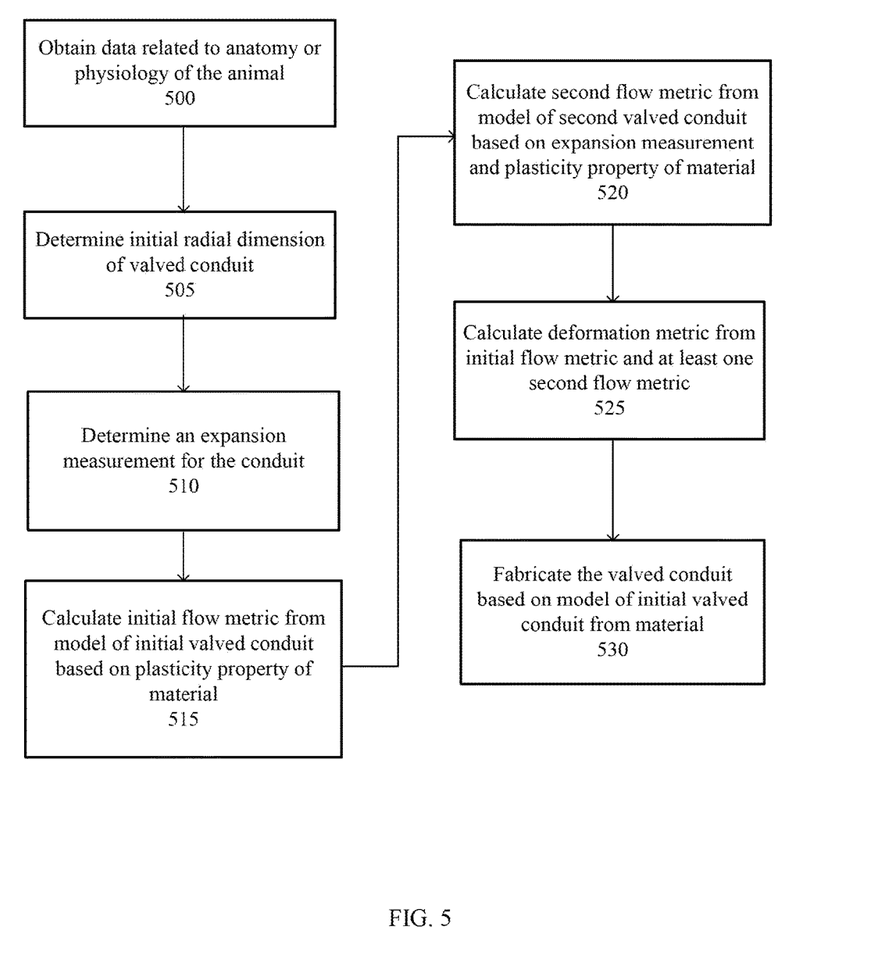
FIG. 5 is a flow chart of a method for fabricating an expandable valved conduit from a plastically deformable material in accordance with the present disclosure.

FIG. 5 is a flow chart illustrating an embodiment of a method for designing an implantable valved conduit composed of a plastically deformable material.

Initially, valved conduit modeling parameters may be provided 500 to the solid-mechanics modeling algorithm, the parameters including data related to the anatomy or physiology of the recipient patient. Examples of such anatomic and/or physiologic data may include a pressure across the valve structure within the valved conduit, a fluid flow rate through the valved conduit, and physical measurements of vascular structures to which the valved conduit may be attached. An initial radial dimension of the valved conduit to be modeled may also be provided 505. Further, data related to the expandability of the plastically deformable material may be provided to the model. Such data may include a yield strength, ultimate tensile strength, elastic modulus, and other mechanical properties of the plastically deformable material. Additionally, a measure of expected patient anatomic growth, or changes to the patient physiology as a response of patient growth, may be determined. The expected patient growth information, along with the data related to the plastic deformability of the valved conduit material, may be used to estimate a desired amount of expandability for the valved conduit. Such expandability data may be provided 510 to the modeling software as one or more expansion measurements for the conduit.

Physical parameters associated with the initially defined valve structure may be provided to the modeling software as well. Such physical parameters may include, without limitation, a conduit length and a conduit wall thickness. Additional physical parameters may be provided to the modeling software that relate to physical dimensions of the valve structure. Some examples of such physical dimensions may be related to the shape and size of valve leaflets that may comprise the valve structure. Non-limiting examples of valve leaflet physical parameters may include one or more of a sinus edge shape, a sinus edge perimeter length, a fan edge shape, a fan edge perimeter length, a height, a fan structure height, a baseline width, and a commissure length. A valve structure modeling computation may then create an initial mathematical model of the initial valved conduit related to the physical and mechanical properties of the valved conduit as initially defined.

The initial model representing the initial valved conduit may then be used in a fluid flow simulation algorithm to determine the characteristics of fluid flow through the initial valved conduit. One or more one or more initial fluid flow metrics including, without limitation, a fluid velocity profile, a fluid pressure profile, and a fluid volumetric flow profile may then be calculated 515 by the fluid flow simulation algorithm. One or more plastic deformability characteristics of the material may also be used in such a fluid flow simulation algorithm in addition to the anatomic and/or physiological data from a patient, the initial proposed radial dimension of the conduit, and physical metrics associated with the valve structure.

Once the initial fluid flow metrics have been calculated 515, the initial mathematical model representing the initial valved conduit may be altered to provide at least a second mathematical model representing at least a second valved conduit. The at least second valved conduit model may differ from the initial valved conduit model in a variety of ways, including, but not limited to, radial dimension of the conduit, valve leaflet physical parameters, expansion measurements of the material, and one or more measures related to the plasticity properties of the material (such as a change in stress or strain characteristics of the materials). One or more second fluid flow metrics may then be calculated 520 by the fluid flow simulation algorithm based on the at least second model of the valved conduit.

It may be appreciated that the fluid flow simulation algorithm may be sequentially applied to additional valved conduit models, each succeeding model representing a succeeding valved conduit that has been altered in some manner from a preceding valved conduit. Thus, for example, a series of valved conduits may be modeled that may differ only in their conduit radial dimensions. Such a series may represent a radial change of an implanted valved conduit over time as the patient grows and the conduit expands to accommodate the patent growth. The change in radial dimension of the valved conduit over time may be simulated by the fluid flow simulation algorithm as a change in the fluid flow metrics associated with each succeeding conduit configuration analyzed thereby.

Once a sequence of fluid flow metrics have been obtained, including the initial fluid flow metric and the at least second fluid flow metric, a deformation metric may be calculated 525. The deformation metric may be calculated from the multiplicity of fluid flow metrics in any number of ways, including, without limitation, an arithmetic mean of fluid flow metrics, a geometric mean of fluid flow metrics, a harmonic mean of fluid flow metrics, or a weighted average of fluid flow metrics. A weighted average of fluid flow metrics may be calculated as a sum of fluid flow metrics, each weighted by some weighting factor. In one non-limiting example, a weighting factor may be derived from a flow efficiency metric or cost function associated with the effectiveness of fluid flow through a valved conduit structure having a particular set of characteristics, such as radial dimension. Efficiency may be based on a fluid flow rate, an open area within the valve structure during flow, or a measure of regurgitant flow.

At the completion of the optimization calculations, a valved conduit may be fabricated 530 from the plastically deformable material using physical characteristics of the conduit and valve structure as supplied to the initial model of the valved conduit if the calculated deformation metric is greater than or equal to an acceptance value. Some non-limiting examples of such acceptance values may incorporate values calculated for one or more of a regurgitation fraction, an open orifice area, and a percent leaflet/wall contact measure. A regurgitation fraction may measure the ratio of fluid back-flow through a valve in a closed state to the fluid forward-flow through the valve in an open state. An open orifice area may be calculated at a percent of a cross-sectional area of the conduit lumen not occluded by the valve structure when the valve structure is in an open position. An additional measure of conduit patency may include a measure of the fraction of a valve structure leaflet in contact with an inner surface of the conduit (compared to total leaflet area). Some examples of an acceptance value may include a regurgitation fraction less than or equal to about 30%, an open orifice area greater than or equal to about 80%, or a leaflet/wall contact value of less than or equal to about 15%.

While an implanted valved conduit fabricated from a plastically deformable material may be able to expand as the patient grows, thereby providing some long term treatment, it may be possible that a single plastically deformable valved conduit may not be sufficient to assist a patient from neonatal size to full adult size. In such an instance, it may be necessary to replace an initial valved conduit with a second valved conduit capable of expanding from an intermediate patient age to full adulthood. A plastically deformable valved conduit may be replaced in situ without the need for excising the original and replacing it with a second valved conduit.

Figure 6:
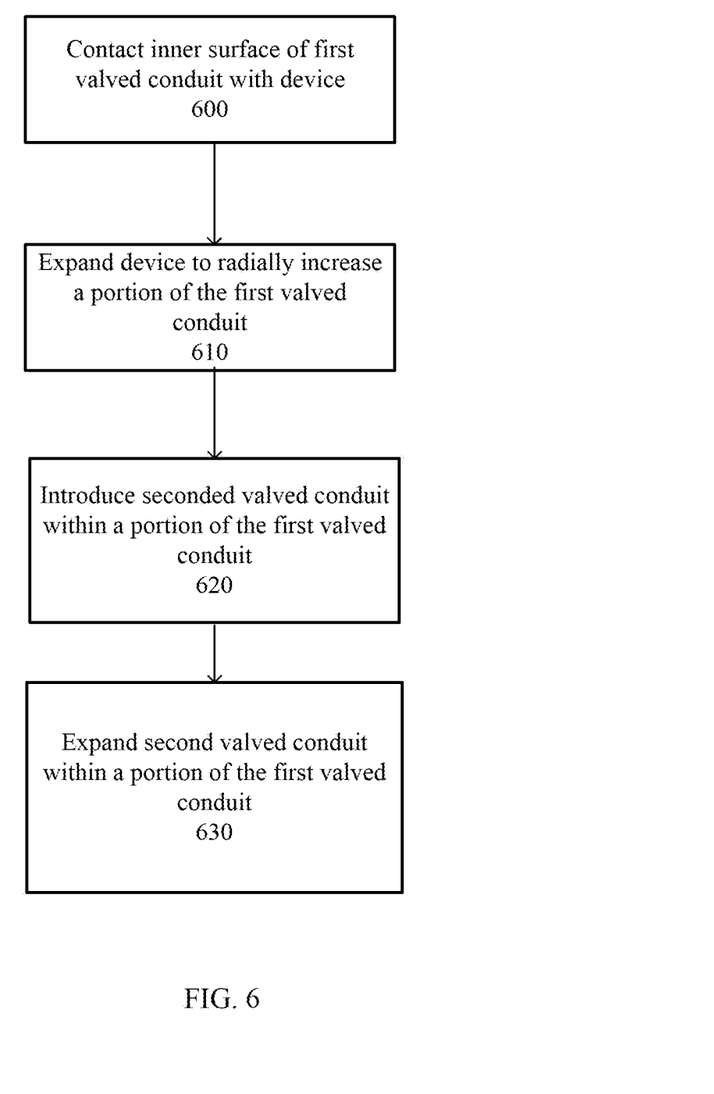
FIG. 6 is a flow chart of a method for replacing a first expandable valved conduit with a second expandable valved conduit in accordance with the present disclosure.

FIG. 6 is a flow chart of one method that may be used to replace an implanted first expandable valved conduit with a second expandable valved conduit.

As disclosed above, a first expandable valved conduit may be unable to assist a patient after some period of patient growth. In one non-limiting example, the conduit may radially enlarge to an extent that the valve structure may no longer efficiently regulate blood flow. The first valved conduit may not have expanded to its fully expanded state when valve structure inefficiency may become apparent. Under such conditions, the first valved conduit may be replaced by a second valved conduit by introducing the second valved conduit within the first valved conduit and expanding the second in situ. Specifically, an expansion device, such as a balloon catheter, may be introduced into the vasculature so that the expansion device contacts 600 an inner surface of the first valved conduit. The expansion device may then be expanded 610 within the first valved conduit thereby radially increasing at least a portion of the first valved conduit. A second valved conduit may then be introduced 620 within at least a portion of the expanded first valved conduit. The second valved conduit may be introduced using the same expansion device as used to expand the first valved conduit while the first valved conduit is expanded. Alternatively, the second valved conduit may be introduced 620 by the use of an alternative device. Once the second valved conduit has been emplaced, the second valved conduit may also be expanded 630 to provide a valve structure capable of regulating fluid flow through the conduit.

EXAMPLES

Example 1

A First Plastically Deformable Material Usable in an Implantable Conduit

Figure 7A:
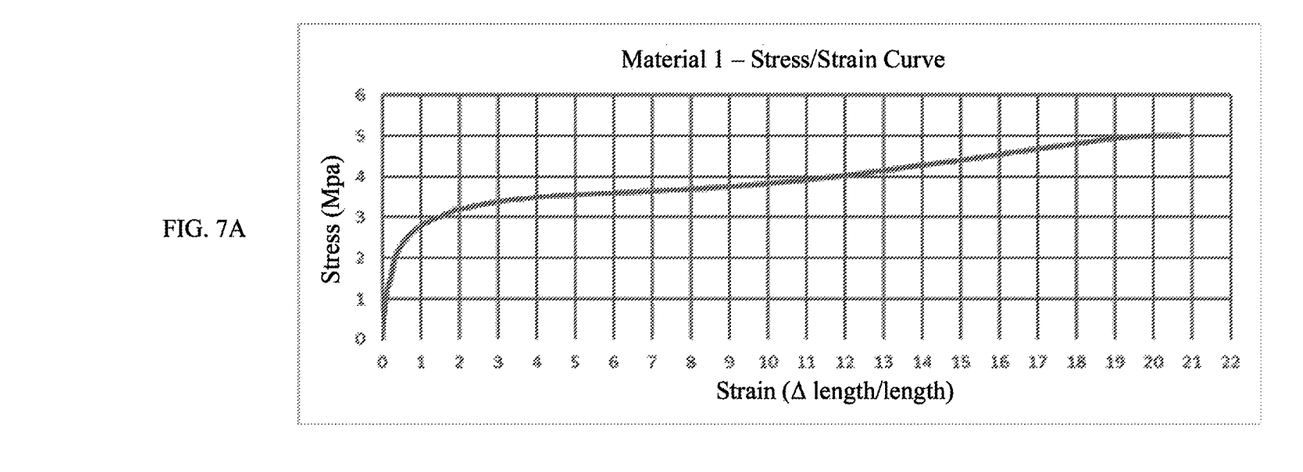
FIGS. 7A and 7B are stress/strain curves obtained for two exemplary plastically deformable materials, respectively, that may be used in a valved conduit in accordance with the present disclosure.

FIG. 7A depicts the stress/strain curve of a first plastically deformable material that may be used to fabricate a plastically deformable and implantable conduit. The material has an average yield strength of about 2.1 MPa and an ultimate tensile strength of about 5 MPa. The material further demonstrates elastic deformation below the yield strength, characterized by an average elastic modulus of about 5.9 MPa. At the section of the stress/strain curve where the material transitions from the elastically deformable mode to the plastically deformable mode, the material demonstrates an average 36% elongation above the original length at the yield stress point. Such a material may be favorably used for a plastically deformable conduit capable of expanding to meet the needs of a growing anatomical structure due to the extended region of the stress/strain curve indicating plastic deformability as opposed to elastic deformability.

Example 2

A Second Plastically Deformable Material Usable in an Implantable Conduit

Figure 7B:
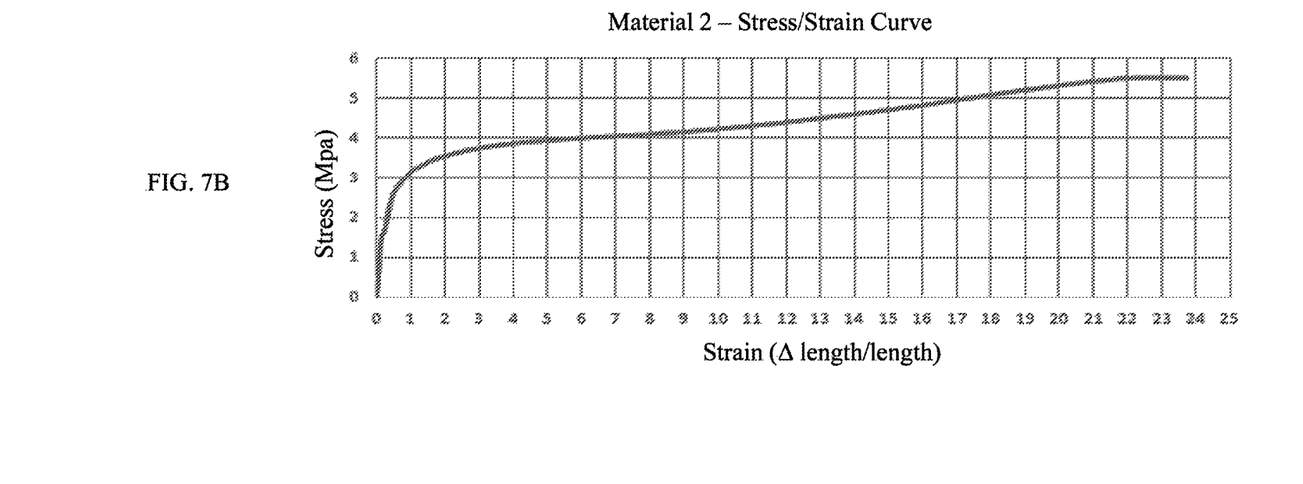

FIG. 7B depicts the stress/strain curve of a second plastically deformable material that may be used to fabricate a plastically deformable and implantable conduit. The material demonstrates an average yield strength of about 1.7 MPa and an ultimate tensile strength of about 5.5 MPa. The material also has a region of elastic deformation below the yield strength characterized by an average elastic modulus of about 7.4 MPa. At the section of the stress/strain curve where the material transitions from the elastically deformable mode to the plastically deformable mode, the material demonstrates an average 24% elongation above the original length at the yield stress point. Such a material may be favorably used for a plastically deformable conduit capable of expanding to meet the needs of a growing anatomical structure due to the extended region of the stress/strain curve indicating plastic deformability as opposed to elastic deformability.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity. It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. An implantable device configured to be plastically deformed using a balloon catheter, the implantable device comprising a fluoropolymer conduit having a yield strength of 0.1 MPa to 3.0 MPa, an ultimate tensile strength greater than 4 MPa, and an internode distance of 10 microns to 60 microns at conditions suitable for implantation into a human or animal.

2. The implantable device of claim 1, wherein the fluoropolymer conduit has a thickness of 0.01 mm to 2 mm.

3. The implantable device of claim 1, wherein the fluoropolymer conduit has a density of 0.2 mg/mm$^3$ to 2 mg/mm$^3$ and an ultimate tensile strength of 5.0 MPa to 5.5 MPa.

4. The implantable device of claim 1, wherein the fluoropolymer conduit has a radial expandability of 20% to 200% above an initial conduit radius.

5. The implantable device of claim 1, wherein the fluoropolymer conduit has a longitudinal expandability of 10% to 200% above an initial conduit length.

6. The implantable device of claim 1, wherein the fluoropolymer conduit comprises at least a first layer and at least a second layer.

7. The implantable device of claim 1, wherein the fluoropolymer conduit further comprises a valve structure.

8. The implantable device of claim 1, wherein the fluoropolymer conduit is configured to be implanted into an adult patient at risk for or having vascular stenosis.

9. The implantable device of claim 1, wherein the fluoropolymer conduit is configured to be implanted into a pediatric patient.

10. The implantable device of claim 1, wherein the fluoropolymer conduit has a radial expandability of 100% to 400% above an initial conduit radius.

11. The implantable device of claim 1, wherein the conditions suitable for implantation into a human or animal are normal physiological conditions.

12. The implantable device of claim 1, wherein the conditions suitable for implantation into a human or animal comprise a temperature of 20 to 40 degrees Celsius.

13. The implantable device of claim 1, wherein the device is implanted into a human.

14. The implantable device of claim 1, wherein the fluoropolymer conduit has a radial expandability of 50% to 200% above an initial conduit radius.

15. The implantable device of claim 1, wherein the yield strength is from 2.5 MPa to 3.0 MPa, the ultimate tensile strength is greater than 5 MPa, and the internode distance is from 10 microns to 40 microns; and wherein the fluoropolymer conduit has a thickness of 0.2 mm to 2 mm and a radial expandability of 100% to 200% above an initial conduit radius.

16. An implantable device comprising a fluoropolymer conduit having a yield strength of 0.1 MPa to 3.5 MPa, an ultimate tensile strength greater than 4 MPa, and an internode distance of 10 microns to 60 microns at conditions suitable for implantation into a human or animal.

17. The implantable device of claim 16, wherein the implantable device is configured to be plastically deformed using a balloon catheter.

* * * * *